United States Patent [19]

Kelman

[11] 4,370,760

[45] Feb. 1, 1983

[54] ANTERIOR CHAMBER INTRAOCULAR LENS

[76] Inventor: Charles D. Kelman, 269-70 Grand Central Pkwy., Floral Park, N.Y. 11005

[21] Appl. No.: 247,570

[22] Filed: Mar. 25, 1981

[51] Int. Cl.³ ............................ A61F 1/16; A61F 1/24
[52] U.S. Cl. ........................................................ 3/13
[58] Field of Search ......................................... 3/13, 1

[56] References Cited

U.S. PATENT DOCUMENTS

| | | | |
|---|---|---|---|
| 4,159,546 | 7/1979 | Shearing | 3/13 |
| 4,174,543 | 11/1979 | Kelman | 3/13 |
| 4,261,065 | 4/1981 | Tennant | 3/13 |
| 4,316,293 | 2/1982 | Bayers | 3/13 |
| 4,328,595 | 5/1982 | Sheets | 3/13 |

OTHER PUBLICATIONS

"Experience with Twelve Cases of Intra-Ocular Anterior Chamber Implants for Aphakia" by J. Boberg-Ans, British Journal of Ophthalmology, vol. 45, No. 1, Jan. 1961, pp. 37–43.

Covered Bridge an Update on Lens Implantation (Book) by John H. Sheers, 1977, pp. 5–13, "Barraquer" Lens in Fig. 11.

The Lindstrom Centrex Style 20 Posterior Chamber Lens, Advertisement Brochure by Surgidev Corp., 1421 State St., Santa Barbara, Calif.

Primary Examiner—Ronald L. Frinks
Attorney, Agent, or Firm—Henry Sternberg

[57] ABSTRACT

An intraocular lens for use as an artificial lens implant anteriorly of the iris which has at least a pair of position fixation elements providing a multi-point support for the lens. The position fixation elements are constructed and arranged for sufficient flexibility to permit a single lens to have the capability of being used as an implant in eyes with anterior chamber diameters of a substantial variety in sizes, thereby minimizing the inventory of lenses necessary to be maintained in operating rooms.

29 Claims, 5 Drawing Figures

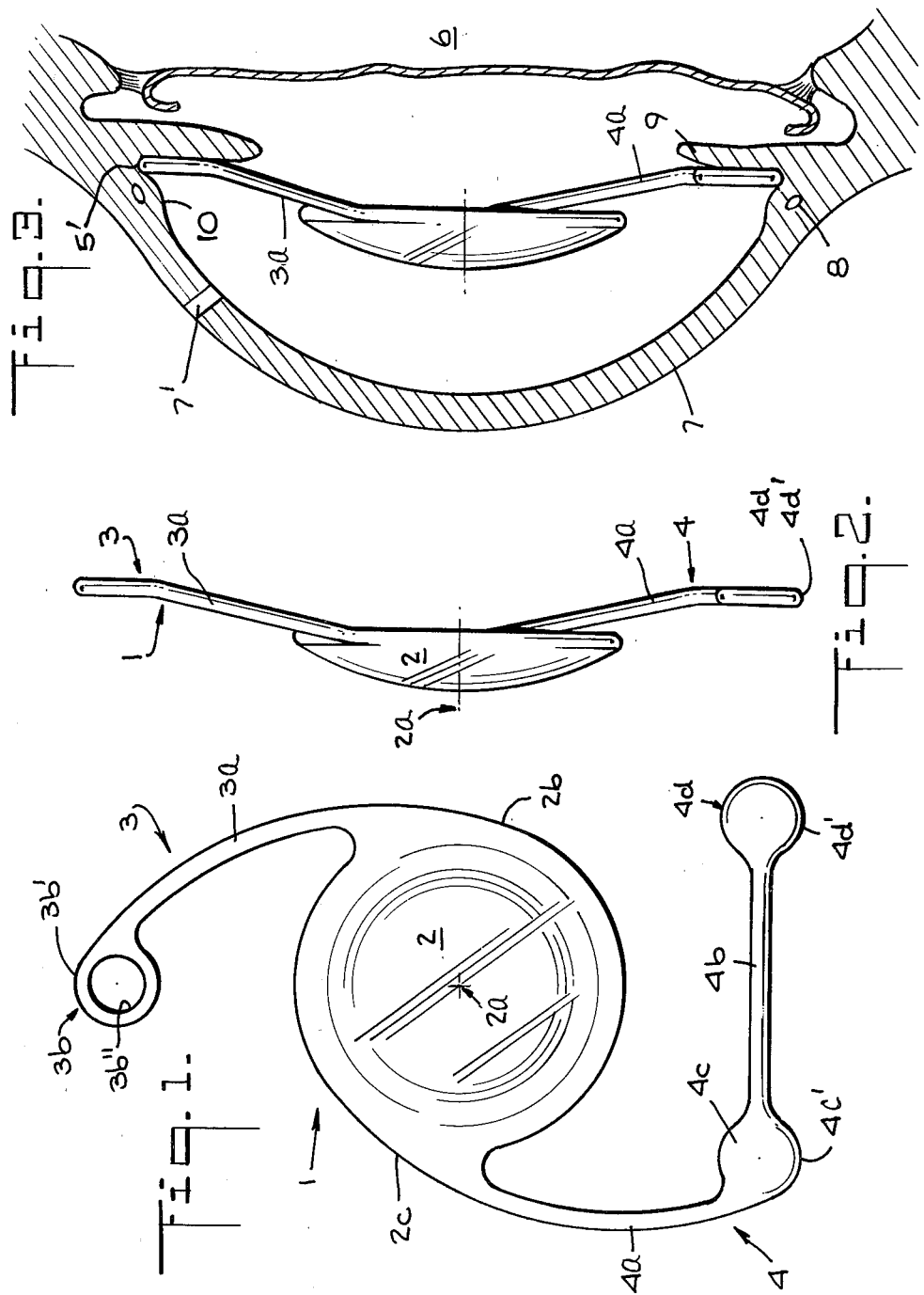

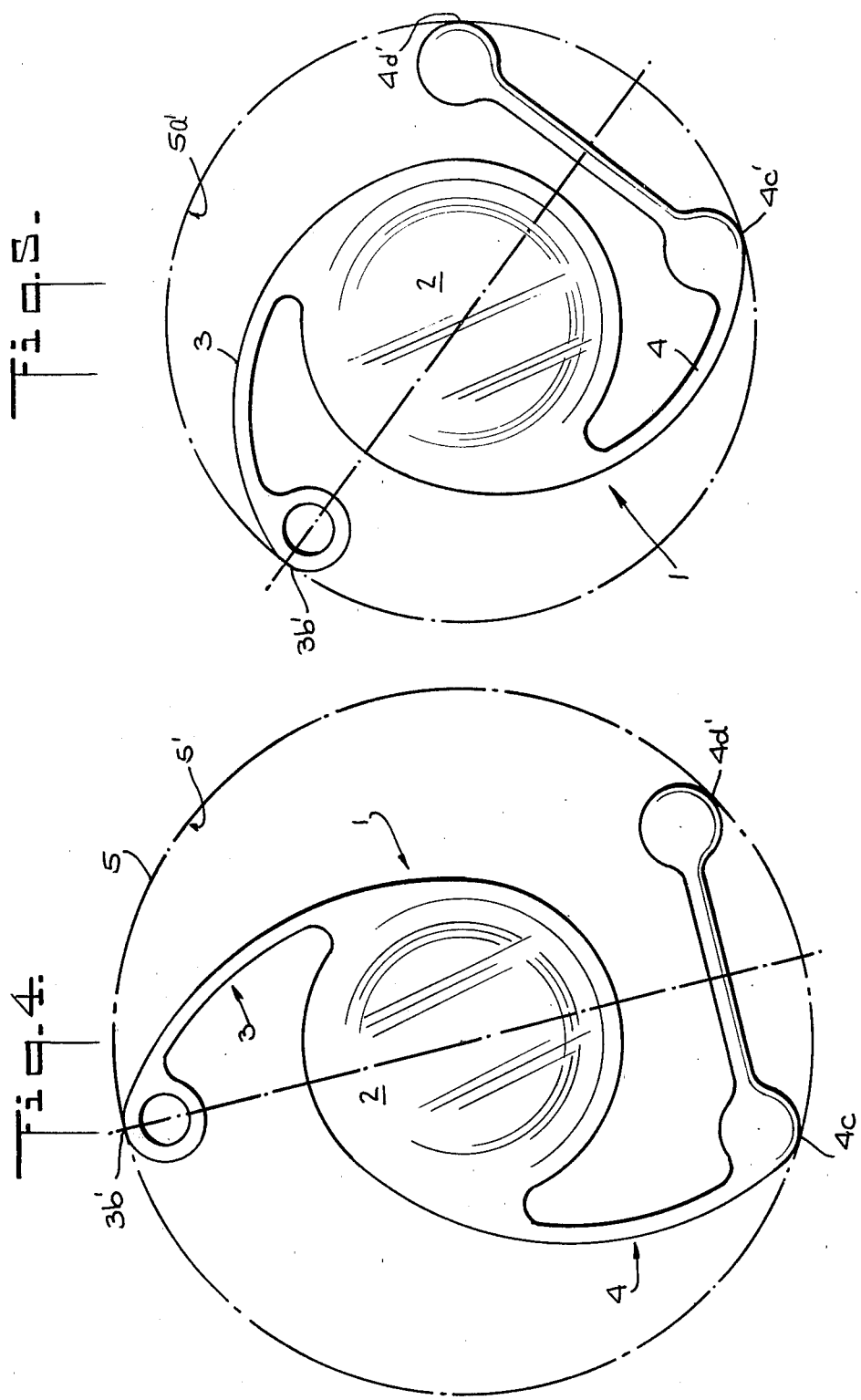

ANTERIOR CHAMBER INTRAOCULAR LENS

BACKGROUND OF THE INVENTION

This invention relates to intraocular lenses for implantation in the anterior chamber of a human eye and more particularly to an intraocular lens having position fixation elements whose effective size is variable so as to permit use of a lens of one size in human eyes of varying size.

The implantation of an intraocular lens is a well known and widely used technique for restoring vision after cataract surgery. The natural structure of the eye furnishes a variety of locations for fixing the position of an intraocular lens in the eye. For example, an intraocular lens can be supported anteriorly of the iris, between the scleral spur and the iris, as disclosed in my U.S. Pat. Nos. 4,174,543 and 4,092,743. Alternatively, an intraocular lens can be supported posteriorly of the iris as disclosed, for example, in U.S. Pat. No. 4,159,546 to Shearing. In practice, anterior chamber lenses are the easiest to implant because the anterior chamber angle can be viewed by the surgeon while he seats the position fixation members therein. This, of course, is not the case with posterior chamber lenses, since they seat behind the iris.

Lens implantations are not only extremely difficult and delicate operations but the use of the currently available anterior chamber lenses, even by highly skilled surgeons, entails a number of disadvantages. One of these is that due to the different sizes of the eyes of different patients a sizable inventory of lenses is currently required by the surgeon to be immediately available in the operating room during the operation. Since the internal diameter of the anterior chamber angle, that is the diameter of the groove formed between the iris and the scleral spur, varies from patient to patient, (generally within a range of 11.5 thru 14.0) millimeters, the lenses currently available are manufactured in half-millimeter increments within that range which is the normal size range for human eyes. Thus lenses are currently available with diameters of 11.5, 12.0, 12.5, 13.0, 13.5 and 14.0 millimeters. Many of these lenses are furthermore available in powers varying from 14.50 thru 22.00 diopters in one diopter increments at the low and high end of the scale and in half diopter increments in the mid-range of that scale. It is very difficult with existing instrumentation to precisely measure the diameter of the anterior chamber angle in which the anterior chamber lens will be seated, prior to the time when the patient is actually in the operating room and an incision has been made. Thus, for each half-diopter increment in the aforesaid mid-range, the surgeon must have available in the operating room seven lenses of different size. It is only after the incision has been made that the most accurate known method for measuring the anterior chamber angle diameter, namely the dip-stick method, can be used.

Once the internal diameter of the anterior chamber has been measured accurately, the surgeon chooses from his inventory of differently dimensioned lenses that lens which most nearly approximates the measured dimension.

Anterior chamber intraocular lenses are known which exhibit some degree of flexibility. Usually the flexibility is for the purpose of compensating for tolerance error in the dimension of the lens, for measurement error on the part of the surgeon, for permitting some flexure in response to normal deformation of the eyeball, or, since lenses commonly are manufactured in half millimeter sizes, for allowing for differences between actual lens size and anterior chamber angle diameter should the angle or groove diameter fall somewhere between two discrete lens sizes. For example, my U.S. Pat. No. 4,092,743 describes an anterior chamber intraocular lens in which the three-point position fixation element is sufficiently flexible to compensate for small differences, up to about one-half millimeter, between the diameter of the groove in the eye in which the lens is to be implanted and the size of the lens in its undeformed condition. Also, my U.S. Pat. No. 4,147,543 discloses a four-point anterior chamber lens which can be deflected along lines drawn diagonally through its four contact points. Such deflection is stated to be in response to the "normal distortions of the eyeball."

Since the latter lenses are intended to deflect only to the extent required to compensate for normal distortions of the eyeball so as to minimize the distortion-related trauma sometimes attributable to an intraocular lens implant, a lens of proper size i.e. one which has a dimension approximating as closely as possible the measured groove dimension must be used to achieve good results. Since the lenses come in discrete sizes and since it is extremely unlikely that the diameter of the anterior chamber angle in the eye will match exactly one of those discrete sizes, the optimum lens fit is hardly ever achieved with known anterior chamber lenses.

The known anterior chamber lenses which have flexure capability, have such capability for an entirely different purpose and to a substantially different degree than is the case with the lens according to the instant invention. None of the known anterior chamber lenses, are capable of minimizing the lens inventory in the operating room to the extent of the instant invention which provides for a single anterior chamber lens adapted to fit all eyes within the normal size range.

Posterior chamber intraocular lenses, on the other hand, have for some time now been made flexible enough to fit all normal posterior chambers. Since, however, posterior chamber lenses, particularly when implanted after extra capsular cataract removal, can be seated in the capsule i.e., in a membrane which is relatively inert in that it has no nerve endings and no blood vessels, and which can therefore readily withstand punishment imposed by seating therein of springy position fixation elements, the forces exerted by, and the length of the contact areas of, the latter, are not nearly as critical in the posterior chamber capsule as in the anterior chamber. In this connection it should also be remembered that surrounding the anterior chamber angle in the vicinity of the scleral spur is the trabecular meshwork which normally pumps fluid out of the eye into Schlemms' canal, which canal, in turn, peripherially surrounds the trabecular meshwork. Any undue pressure on the anterior chamber angle in the vicinity of the scleral spur, such as may be caused by a lens implant, may interfere with the proper functioning of Schlemms' canal and may cause pain and inflammation.

While some slight interference with the functioning of the canal does not appear to be detrimental, more substantial interference as would be occasioned by anterior chamber lenses having seating portions extending over substantial peripheral regions of the anterior chamber angle and thus sealing substantial portions of the trabecular meshwork and possibly even transmitting pressure against substantial regions of Schlemms' canal, would be detrimental. By limiting such contact to regions aggregating less than 10% of the periphery of the anterior chamber angle such detrimental interference with the functioning of Schlemms' canal may be minimized.

From the foregoing it will be seen why known posterior chamber lenses have not been used and are not useful in the anterior chamber. Thus, known posterior chamber lenses, such as the Simcoe posterior chamber lens having two or three very long and very flexible haptic loops which are curved to match their respective arcs of contact with the ciliary sulcus, so as to distribute pressure evenly over as large a surface area as possible, so as to avoid focused single-point pressure, would have a deliterious effect on the functioning of Schlemms' canal and therefore should not be used in the anterior chamber. Most other known posterior chamber lenses which exhibit flex capability sufficient to operate within the size ranges specified herein, are not of three-point contact construction and therefore do not exhibit the stability which known anterior chamber lenses are able to provide. Many posterior chamber lenses including the 2- and the 3-leg Shearing-type posterior lenses, have a construction which results in their optic portion being displaced axially when the legs of the lens are squeezed from their undeformed condition into their deformed condition, i.e. their condition after the lens has been seated in the posterior chamber. Since anterior chamber lenses however are positioned between the iris and the cornea, substantial axial movement of this type cannot be tolerated since the distances to the iris on the one hand and to the cornea on the other hand are relatively small. Therefore, if the optic, after implant surgery, is too close to the cornea, normal distortions of the eyeball can result in contact by the optic with the endothelial layer of the cornea risking severe injury to the cornea. Furthermore, many of the known posterior as well as anterior chamber lenses frequently require a deflection force substantially in excess of one gram, which force will, in the implanted lens, determine the amount of pressure exerted against the tissues of the eye in which the lens is seated. The amount of pressure, will depend not only on the force but also on the area of contact between the position fixation elements of the lens and the tissue in which they are seated. Substantially greater pressures are acceptable for seating in the capsular sulcus in the posterior chamber than are acceptable for seating in the anterior chamber angle. In the lens according to the present invention the contact areas are limited and are preferably substantially point-contact. Thus, the force exerted by the position fixation elements of the lens according to the present invention is transmitted at preferably three or four (not shown) discrete points only and is not distributed over large surface areas at any of these points. A force of less than one gram has been found to show good results. If we assume a contact area of one square millimeter then the pressure will of course be less than one gram per square millimeter. Contact areas in the order of 2 or 3 square millimeters will of course even further substantially reduce the pressure on such tissues.

SUMMARY OF THE INVENTION

In accordance with the present invention a novel anterior chamber lens structure is provided.

The structure includes a lens adapted to be implanted in the groove formed between the iris and the scleral spur in the anterior chamber of human eyes of different anterior chamber diameters. The lens includes an optic, and a pair of lateral position fixation elements connected with the optic. One of the position fixation elements includes a first contact portion adapted to seat in the upper portion of the groove, while the other position fixation element includes a second contact portion adapted to seat in the lower portion of the groove. The first and second contact portions are constructed and arranged for relative movement therebetween to assume a first fully extended position in which they are spaced apart a distance substantially equal to the largest anterior chamber diameter within the range of anterior chamber diameter sizes most commonly exhibited by human eyes, and a plurality of second positions corresponding to the different anterior chamber diameters of different eyes within that range. The lens structure also includes means for urging the contact portions in a direction to assume said fully extended position so as to maintain said contact portions seated in the respective groove portions upon said lens being implanted in an eye having an anterior chamber diameter of any size within said range. Consequently, the position fixation elements will properly position the lens in the anterior chamber of any eye exhibiting any anterior chamber diameter within such range.

It is an object of the present invention to provide an intraocular lens capable of being implanted in the anterior chamber angle of an eye having an internal diameter anywhere in the normal size range for the majority of human eyes.

It is another object of this invention to provide an anterior chamber lens which will fit any one of a series of eyes of different dimensions without excessive pressure being exerted by the lens against the anterior chamber angle in which it is seated.

It is a further object of this invention to provide an anterior chamber lens, having the aforesaid characteristics, which will minimize the risk of contact between the lens and the cornea during and after implantation.

For a better understanding of the present invention, together with other and further objects thereof, reference is made to the following description taken in connection with the accompanying drawings, and its scope will be pointed out in the appended claims.

BRIEF DESCRIPTION OF THE DRAWINGS

FIG. 1 is a plan view of an embodiment of the present invention intended for fixation in the anterior chamber of the eye.

FIG. 2 is a side view of the intraocular lens structure of FIG. 1.

FIG. 3 is a sectional view of an eye with the intraocular lens structure of FIG. 1 fixed therein and shown in side elevation in reduced size.

FIG. 4 is a plan view of the intraocular lens structure of FIG. 1 seated in the anterior chamber angle of a relatively large eye.

FIG. 5 is a plan view of the intraocular lens structure of FIG. 1 seated in the anterior chamber angle of a relatively small eye.

DESCRIPTION OF THE PREFERRED EMBODIMENTS

According to the preferred embodiment of this invention there is provided an anterior chamber intraocular lens having a central optic portion 2 with an optical axis 2a, as seen in FIGS. 1, 2 and 3 of the drawings.

Extending from a first peripheral portion 2b of the optic 2 is a first position fixation element 3. The optic has a second peripheral portion 2c spaced from said first mentioned peripheral portion and generally at opposite sides of the optical axis 2a with respect to said first mentioned peripheral portion. Extending from said second peripheral portion 2c of optic 2 is a second position fixation element 4. The position fixation elements 3, 4 extend from the optic 2 generally tangentially and in generally opposite directions with respect to each other. Position fixation element 3 has a curved leg portion 3a with a free end 3b forming a contact surface 3b', while position fixation element 4 has a curved leg portion 4a and an arm portion 4b extending transversely from the distal end of leg portion 4a so as to extend partly peripherally of said optic. The leg portions are so configured that the concave side of the curved leg 4a faces generally toward the concave side of leg 3a. Position fixation element 4 has a pair of contact surfaces for contacting and seating in the anterior chamber angle 5' of an eye in the vicinity of the scleral spur 10. One contact surface 4c' is in the region where the leg 4a connects with arm 4b, and the other contact surface 4d' is located at the free end 4d of transverse arm 4b.

Leg portions 3a and 4a are also oblique and respectively connect the corresponding end portions 3b and 4c with the lens body 2. End portions 3b, 4c and 4d are located substantially in coplanar relationship in a plane which is perpendicular to the optical axis 2a and is spaced posteriorly at the optic 2. The oblique leg portions 3a and 4a thus extend between the optic 2 and the said plane containing end portions 3b, 4c and 4d.

According to the aforesaid construction, there is formed an anterior chamber lens 1 which exhibits three-point fixation capability. One or both of the position fixaton elements, or legs, 3 and 4 is resilient i.e. springy, such that it will return to its original undeformed condition shown in FIG. 1 after compression or extension away from the illustrated configuration. The anterior chamber lens according to the instant invention has the important capability of being able to be deformed in such manner and to such an extent as to be safely and easily accommodated in anterior chamber angles having a wide range of diameters. Thus, according to the preferred embodiment of the instant invention the anterior chamber lens 1 is manufactured in its entirety as a unit of a single piece of polymethylmethacrylate, or similar biologically inert plastic material. Alternatively, the elements 3, 4 may be connected by adhesive or ultrasonic welding or any other connection method known in the art. The cross-sectional shape, diameter and length of the position fixation elements 3 and 4 as well as the angles at which they project from optic 2 and the amount of curvature of the legs 3a and 4a are all such as to facilitate a combined flexure of those elements sufficient to permit substantial relative movement between contact surfaces 4c' and 4d', on the one hand, and contact surface 3b' on the other hand. Because of the greater stability of lenses having three-point-contact over those having two-point-contact, the former are much preferred to the latter in those regions of the eye in which they are capable of being used. Lenses with three or more contact points are more difficult to use in the posterior chamber because of the inaccessibility of the seating region in the posterior chamber and the necessity to dilate the pupil substantially in order to insert the larger lens into the posterior chamber.

Preferably, the legs 3 and 4 have their end portions 3b and 4b located in a plane which is parallel to and approximately 1 mm behind the plane of the posterior face of optic 2. By way of example, I will refer to a lens which in its undeformed condition, as seen in FIG. 1, fits within an imaginary 14 mm diameter circle (not shown), with its three contact surfaces 3b', 4c' and 4d' each touching that circle and each making substantially a point contact therewith. The lens, in the example, has a 6 mm diameter optic. The legs 3 and 4 are of generally round cross-section approximately 0.320 mm in diameter. Arm 4b is straight and is located approximately 5.46 mm from the optical axis 2a and is approximately 6.14 mm long as measured center to center of the radii of curvature of the contact surfaces 4c' and 4d' respectively. The legs 3a and 4a are both curved in generally the same direction about the periphery of the optic 2, and the radius of curvature of each of the legs 3a and 4a is approximately 6.80 mm while the radius of curvature of each of the contact surfaces 3b', 4c' and 4d' is approximately 0.75 mm. The lens is dimensioned such that a line drawn through the center of curvature of contact surface 3b' and through the optical axis 2a bisects the arm 4b. It will be seen that each of the contact surfaces is located on an element which is cantilevered from the optic. Leg 3a is cantilevered and extends generally tangentially from the periphery of optic 2. Leg 4a is cantilevered and also extends generally tangentially from optic 2, and arm 4b is cantilevered from and extends generally transversely from end portion 4c and generally circumferentially of, and spaced from the optic 2.

A lens constructed in the manner just described and having the dimensions described above has been found to exhibit the following characteristics when a force was applied between surface 3b', on the one hand, and surfaces 4c' and 4d', on the other hand, so as to deform the lens from the undeformed condition thereof illustrated in FIG. 1, to a first deformed condition such as the one illustrated in FIG. 4 of the drawings, and then to a second even further deformed condition, such as the one illustrated in FIG. 5: A force of approximately one tenth of one gram resulted in a reduction of 3.54 millimeters in the distance between the surface 3b' and the surfaces 4c' and 4d'. A 3.8 millimeter reduction in the distance between those surfaces from the said first undeformed condition to one of said second deformed conditions was accomplished with the application of a force, between said surfaces of approximately two tenths of one gram.

FIG. 4 illustrates the lens according to the preferred embodiment of this invention seated in the anterior chamber angle 5' of an eye having an anterior chamber angle diameter of approximately 13.5 mm, i.e. near the large end of the normal size range for human eyes. Thus, the lens 1, which is preferably 14.0 mm in size i.e. would fit into a circle having a diameter of 14.0 mm, is seen in only slightly deformed condition in FIG. 4 with the contact surface 3b' on the one hand and contact surfaces 4c' and 4d', on the other hand, having been moved somewhat relatively to each other from their undeformed condition illustrated in FIG. 1 to their slightly deformed condition illustrated in FIG. 4. It will be seen that because of the position, shape and size of the contact surfaces 3b', 4c' and 4d', the three-point-contact lens according to the preferred embodiment of this invention contacts the anterior chamber angle at three distinct, relatively widely spaced, locations and that the extent of such contact at each of those locations is substantially limited.

FIG. 5 of the drawings shows the deformation of the same lens 1 accommodated in an anterior chamber angle 5a' having a diameter of approximately 11.5 mm, i.e. a diameter at the small end of the range of normal sizes for human eyes. It will be seen that the configuration, according to the preferred embodiment of the invention, is such that lens 1 remains relatively stable even when implanted in anterior chamber angles of substantially different diameters such as illustrated in FIGS. 4 and 5, respectively. Thus, the contact surface 3b', even in substantially fully deformed condition of the lens shown in FIG. 5, has its center of curvature located on a line which passes through the optical axis 2 and bisects the arm 4b. This results at least partly from rotation of the optic 2 about its optical axis 2a during movement of the contact portions 3b, on the one hand, and 4c and 4d, on the other hand, toward one another. Such rotational movement of the optic takes place in the clockwise directon, as viewed in FIG. 4 of the drawings, when the lens is deformed from its condition illustrated in FIG. 1 to any of the second positions thereof as exemplified by the conditions illustrated in FIGS. 4 and 5.

As is well known, because of the proximity of the cornea 7 to the optic of any anterior chamber lens, it is essential that such optic is maintained spaced from and not be permitted to come in contact with the cornea. This is true both during insertion and seating of the lens in the anterior chamber angle and thereafter. It has been found that the risk of contact with the cornea can be minimized by a lens design which limits to a distance of approximately one millimeter the distance which the optic moves toward the cornea as a result of deflection of the position fixation elements during as well as after implantation. Thus, deformation of the legs 3a and 4a of the lens in order for it to be seated in the anterior chamber angle must not result in movement of the optic toward the cornea a distance substantially in excess of 1 mm otherwise there is increased substantially the risk of contact between the optic and cornea during deformations normally occurring in the eyeball after lens implantation. The lens according to the preferred embodiment of the present invention has its legs 3 and 4 sufficiently flexible and configurated such that axial movement of the optic does not substantially exceed one millimeter in response to deformation of the contact portions 3b, 4c and 4d toward each other from the undeformed condition of the lens illustrated in FIG. 1 to the deformed condition illustrated in FIG. 5.

Also, the lens according to the preferred embodiment of the present invention is constructed and arranged such that during deformation of the springy legs 3 and 4 thereof from the condition illustrated in FIG. 1 to the condition in FIG. 5, the force exerted by each of the respective contact portions 3b, 4c and 4d preferably does not substantially exceed one gram. Since the amount of contact which the surfaces 3b', 4c' and 4d' each make with the tissue at the interior of the anterior chamber angle, is on the order of but certainly not less than approximately one square millimeter, the pressure exerted on the tissue will be less than and will certainly not exceed one gram per square millimeter. Furthermore, the legs 3 and 4 are constructed and arranged such that when positioned in all but the very largest diameter anterior chamber angle, i.e. the maximum size within the aforesaid normal range of sizes, the force exerted by each of the legs 3 and 4 will help to assure that the lens will remain seated within the anterior chamber angle of the eye, yet will not exert excessive pressure, even when used in eyes having an anterior chamber angle diameter of only approximately 11.5 mm.

According to the preferred surgical procedure for seating such a lens, the surgeon would first position contact surfaces 4c' and 4d' in the anterior chamber angle 5a' in the vicinity of the scleral spur of the eye as illustrated for example in FIG. 5 and thereafter with a forceps or similar instrument grasping the leg 3, preferably at opening 3b' thereof, urge the latter in a direction toward the optical axis 2a until the lens is deformed to a somewhat smaller size than the diameter of the anterior chamber angle in question. Then, after tilting the leg 3 toward and into position adjacent the iris 9, release the end portion 3b so as to permit the latter to expand toward and to seat in the corresponding part of the anterior chamber angle 5a' between the iris and the scleral spur, resulting in the lens assuming its fully seated position illustrated in FIGS. 3, 4 and 5, respectively. It will be noted that even in the substantially deformed condition of the lens 1 illustrated in FIG. 5, each of the three spaced contact surfaces 3b', 4c' and 5d', have only very limited areas thereof in contact with the interior peripheral surface of the groove 5a', and that these limited areas of contact aggregate substantially less then 10% of the periphery of the groove 5a'.

While in the foregoing specification an embodiment of the present invention has been set forth in considerable detail for the purpose of making a complete disclosure of the invention, it will be apparent to those skilled in the art that various changes may be made in such details without departing from the spirit and principles of the invention. For example, the leg 3 illustrated above could be replaced with an L-shaped leg such as the leg 4 also illustrated above, so that the lens would then have four contact points instead of three. Also, four contact points could be achieved with four legs similar to the leg 3 above. Many other such changes would of course be apparent to those of ordinary skill in the art and would not depart from the spirit or principles of the invention.

What is claimed is:

1. An intraocular lens adapted to be implanted in the groove formed between the iris and the scleral spur in the anterior chambers of human eyes of different anterior chamber diameters, including:

an optic, a pair of lateral position fixation means connected with said optic, one of said position fixation means including a first contact portion adapted to seat in the upper portion of the groove, the other position fixation means including a second contact portion adapted to seat in the lower portion of the groove, said optic having opposite peripheral portions and said one position fixation means having a first portion extending outwardly from a first of said peripheral portions and said other position fixation means having a first portion extending outwardly from a second of said peripheral portions, at least one of said pair of position fixation means having a second portion extending from the first portion generally transversely thereto and at least partly peripherally of said optic, said second portion of said position fixation means having that part of its peripheral edge which faces said optic spaced from the periphery of said optic and having a free end portion, said first and second contact portions being constructed and arranged for relative movement therebetween to assume a first fully extended position in which said contact portions are spaced apart a distance substantially approximating the largest anterior chamber diameter within the range of anterior chamber diameter sizes most commonly exhibited by human eyes, and a plurality of second positions corresponding to the different anterior chamber diameters of different eyes within said range, said pair of position fixation means being constructed and arranged to undergo said relative movement from said first to any of said second positions thereof while limiting movement of said optic along the optical axis thereof in anterior direction toward the cornea to a distance not substantially in excess of 1.0 mm and to a position in which the optic, after seating of the lens in the anterior chamber groove corresponding to any of said second positions, will be sufficiently spaced from the cornea to minimize risk of contact between the optic and the cornea during normal deformations of the eyeball thereafter, and at least one of said pair of position fixation means being effective to urge said contact portions in a direction to assume said fully extended position so as to maintain said contact portions seated in the respective groove portions upon said lens being implanted in an eye having an interior chamber diameter of any size within said range, whereby said position fixation means properly position the lens in the anterior chamber of any eye exhibiting any anterior chamber diameter within said range.

2. The intraocular lens claimed in claim 1 wherein said urging means is adapted to maintain said contact portions seated in the respective groove portions while not exerting an excessively injurious force on the tissues of such groove portion even where such groove has a diameter which is the smallest anterior chamber diameter within said range.

3. The intraocular lens as claimed in claim 1, wherein said first and second contact portions are constructed and arranged such that in any of said plurality of second positions thereof the surface portions of the anterior chamber groove with which they are in contact when seated therein will have an aggregate peripheral length sufficiently small so as not to interfere with the functioning of Schlemm's canal to any undesirable extent.

4. The intraocular lens as claimed in claim 1, wherein said pair of position fixation means are constructed and arranged to undergo said relative movement from said first to any of said second positions thereof while simultaneously limiting movement of said optic also in posterior direction toward the iris to a position in which the optic, after seating of the lens in the anterior chamber groove corresponding to any of said second positions, will be sufficiently spaced from the iris to minimize risk of contact between the optic and the iris during normal deformations of the eyeball thereafter.

5. The intraocular lens according to claim 1 wherein said second contact portion comprises a pair of spaced contact portions so that the lens will have three-point fixation.

6. The intraocular lens according to claim 1 wherein the distance between first and second contact portions in their first fully extended position is at least 14.0 mm.

7. The intraocular lens according to claim 1 wherein the plurality of second positions correspond to anterior chamber diameters within the range of 11.5 mm to 14.0 mm inclusive.

8. The intraocular lens according to claim 1 wherein one of said pair of position fixation means includes said means for urging and contact portions in a direction to assume said fully extended position.

9. The intraocular lens according to claim 1 wherein each of said pair of position fixation means includes a means for urging said contact portions in a direction to assume said fully extended position.

10. The intraocular lens as claimed in claim 1 wherein said means for urging said contact portions exerts a force not substantially in excess of one gram against the respective groove portions upon said lens being implanted in the eye.

11. The intraocular lens as claimed in claim 3 wherein said contact portions together contact less than 10% of the periphery of the anterior chamber groove in which they are seated.

12. An intraocular lens as claimed in claim 1 in which said first portion of said one position fixation means extends generally tangentially from said first peripheral portion of said optic and said first portion of said other position fixation means extends generally tangentially from said second peripheral portion of said optic.

13. The intraocular lens as claimed in claim 1 wherein said one position fixation means includes:
 (i) a leg portion contiguous to and extending generally laterally outwardly from the periphery of said optic and having a first end portion spaced from said optic, said first end portion including said first contact portion, and
 (ii) an arm portion extending from said first end portion generally transversely to said leg portion and at least partly peripherally of said optic, said arm portion having a free second end portion spaced from said optic and including a third contact portion, and said portion having a medial region between said first and second end portions disposed closer to the optic than either of said first and third contact portions.

14. The intraocular lens as claimed in claim 13 wherein each of said pair of position fixation means extends generally tangentially from the corresponding peripheral portion of the optic.

15. The intraocular lens as claimed in claim 14 wherein said other position fixation means extends generally tangentially from said optic and said second contact portion is substantially bisected by an imaginary extension of a diameter of the optic which substantially bisects said transverse arm portion of said one position fixation means.

16. The intraocular lens as claimed in claim 14 wherein said other position fixation means and said leg portion of said one position fixation means are each arcuate and are each curving in the same general direction around the periphery of the optic.

17. The intraocular lens as claimed in claim 13 wherein said first and third contact portions at opposite ends of said arm have rounded contact surfaces for limiting their engagement with the groove in the eye when seated therein.

18. The intraocular lens as claimed in claim 13, wherein said arm portion is cantilevered from said leg portion and said leg portion is cantilevered from said optic so as to facilitate flexing of said one position fixation means.

19. The intraocular lens as claimed in claim 13 wherein each of said position fixation means is springy for permitting movement of said second as well as of said first and third contact portions toward and away from the optical axis of said optic.

20. The intraocular lens as claimed in claim 13 wherein each of said contact portions is rounded and is spaced from the peripheral surface of said optic so as to be moveable relative thereto.

21. The intraocular lens as claimed in claim 10 wherein each of said position fixation means is connected at one of its ends to said optic, is bowed in a direction generally conforming to the curvature of the periphery of said optic and otherwise is spaced therefrom along its entire length so as to permit said contact portions to flex towards the optic in response to the application of a force applied thereto in a direction generally toward said optic.

22. The intraocular lens as claimed in claim 1 wherein said optic has a convex anterior surface, and a substantially flat posterior surface defining a first plane and said pair of lateral position fixation means having their free end portions located in a second plane spaced posteriorly to said first plane.

23. The intraocular lens as claimed in claim 13 wherein said pair of position fixation means are configurated and arranged such that said first and third contact portions of said one position fixation means are spaced, in undeformed condition of said position fixation means, a diametral distance of approximately 14 mm from said second contact portion of said other position fixation means and that a force applied between said second contact portion of said other position fixation means, on the one hand, and said first and third contact portions of said one position fixation means on the other hand, sufficient to move said contact portions toward each other a distance of approximately 2.5 mm will not result in movement of said optic along said optical axis thereof, in posterior to anterior direction, a distance substantially in excess of 1.0 mm.

24. The intraocular lens as claimed in claim 23 wherein said pair of position fixation means are arranged and constructed such that said optic will undergo some rotational movement about its optical axis in response to said force being applied between the said pair of contact portions of said one position fixation means on the one hand and the contact portion of said other position fixation means on the other hand.

25. The intraocular lens as claimed in claim 1 wherein the optic and the pair of position fixation means are formed out of one piece of plastic material.

26. The intraocular lens as claimed in claim 1 wherein said lens is of unitary construction and made of a single piece of polymethylmethacrylate.

27. The intraocular lens as claimed in claim 16 wherein said other position fixation means includes a leg portion intermediate said optic and said second contact portion and said leg and arm portions of said pair of position fixation means are each approximately 0.320 mm in diameter and said leg portions each have a radius of curvature approximately 6.80 mm and all said contact portions have a radius of curvature of approximately 0.75 mm.

28. The intraocular lens as claimed in claim 13 wherein said one position fixation means comprises a leg portion having at its free end said first contact portion and wherein except for connection with said leg portion of said one portion fixation means and said leg portion of said other position fixation means all said contact portions are spaced from and out of contact with said optic when said pair of position fixation means are in said first or in any of said second positions thereof.

29. An intraocular lens adapted to be implanted in the groove formed between the iris and the scleral spur in the anterior chambers of human eyes of different anterior chamber diameters, comprising:
an optic having opposite peripheral portions,
a first and a second position fixation means connected with said optic,
said first position fixation means extending generally tangentially from one of said peripheral portions and including at least one first contact portion adapted to contact the lower part of the groove,
said second position fixation means extending generally tangentially from the other of said peripheral portions, said second position fixation means including at least one second contact portion adapted to contact the upper part of the groove,
said first and second contact portions being movable relative to each other between a first fully extended position in which said contact portions are spaced apart approximately 14 mm and a plurality of second positions corresponding to the different anterior chamber diameters of different eyes, within the range of 11.5 and 14.0 mm, inclusive,
at least one of said pair of position fixation means including resiliently deformable means for urging said contact portions against the respective groove portions with a force not substantially exceeding one gram, in response to said lens being implanted in an eye having an anterior chamber diameter of any size within said range,
said contact portions having seating portions of limited peripheral length such that in response to said lens being implanted in an eye having a anterior chamber diameter within said range said seating portions will, in the aggregate, contact the anterior chamber groove along less than 10% of the periphery of such groove,
said first and second position fixation means being configurated such that movement of said optic in posterior to anterior direction along the optical axis thereof, in response to movement of said contact portions of said first and second position fixation means from said first position thereof to any one of said second positions thereof, will not substantially exceed one millimeter,
whereby said first and second position fixation means will properly position the lens in the anterior chamber of any eye exhibiting any anterior chamber diameter within said range.

* * * * *